United States Patent [19]
Craver et al.

[11] Patent Number: 6,136,017
[45] Date of Patent: Oct. 24, 2000

[54] ONE HANDED INSTRUMENT FOR SPREADING A HEART VALVE

[75] Inventors: Joseph Craver, Atlanta, Ga.; Louis A. Campbell, Austin, Tex.

[73] Assignee: Sulzer Carbomedics Inc., Austin, Tex.

[21] Appl. No.: 09/296,190

[22] Filed: Apr. 23, 1999

[51] Int. Cl.[7] .......................... A61B 17/28; A61B 17/00; A61B 1/32

[52] U.S. Cl. ................................ 606/205; 606/53; 606/1; 606/99; 600/206; 600/209; 600/219; 600/226; 600/235

[58] Field of Search ................................. 606/205, 1, 53, 606/99; 623/2; 600/235, 209, 206, 218, 219, 226

[56] References Cited

U.S. PATENT DOCUMENTS

| | | | |
|---|---|---|---|
| 3,313,294 | 4/1967 | Uddenberg | 128/20 |
| 5,290,292 | 3/1994 | Householder | 606/107 |
| 5,476,510 | 12/1995 | Eberhardt et al. | 623/2 |
| 5,669,919 | 9/1997 | Sanders et al. | 606/148 |
| 5,683,405 | 11/1997 | Yacoubian et al. | 606/158 |
| 5,842,974 | 12/1998 | Stubbs | 600/206 |
| 5,849,024 | 12/1998 | Schellpfeffer | 606/205 |
| 5,906,642 | 5/1999 | Caudillo et al. | 623/2 |

*Primary Examiner*—Linda C. M. Dvorak
*Assistant Examiner*—Jocelyn Debra Ram
*Attorney, Agent, or Firm*—Timothy L. Scott; Philip S. Lyren

[57] ABSTRACT

An instrument for spreading the anterior leaflet of a mitral valve. The surgical instrument is designed to allow a surgeon to grip an instrument with one hand during sizing of the anterior leaflet prior to implantation of an annuloplasty ring in a heart valve. The instrument includes a pair of tines that each have an engagement tip for engaging the *chordae tendinae* proximate an anterior leaflet of a heart valve. The tines are coupled together by a gripping mechanism that may be easily held in one hand, while an annuloplasty ring sizer is held in the surgeon's other hand.

20 Claims, 4 Drawing Sheets

ONE HANDED INSTRUMENT FOR SPREADING A HEART VALVE

FIELD OF THE INVENTION

The present invention relates generally to an instrument for facilitating the implantation of an annuloplasty ring, and particularly to an instrument and method for pulling or stretching out the anterior leaflet of the mitral valve during sizing of the anterior leaflet with an annuloplasty ring sizer.

BACKGROUND OF THE INVENTION

For a variety of reasons, heart valves, such as the mitral valve, can become enlarged. As the mitral valve, for instance, enlarges, the function of the heart can be detrimentally affected. If the valve becomes sufficiently enlarged, cooperating surfaces fail to meet and the valve ceases to function properly leading to severe heart problems or potentially heart failure.

A relatively common surgical procedure designed to correct the enlarged valve involves implantation of an annuloplasty ring. During this procedure, an annuloplasty ring is sewed to the tissue surrounding the subject heart valve. The annuloplasty ring effectively braces or holds the valve at an appropriate size to permit proper functioning of the heart valve.

In the typical procedure, the annuloplasty ring is attached to the tissue surrounding the mitral valve. The size of the anterior leaflet for a given heart valve dictates the size of the annuloplasty ring to be implanted. Accordingly, the anterior leaflet must be measured to permit proper sizing of the annuloplasty ring for a given heart and patient.

Conventionally, the anterior leaflet of the mitral valve is stretched as if it were closed and sized with an annuloplasty ring sizer. The surgeon typically has available several ring sizers having ends of predetermined sizes. Once the given anterior leaflet is matched with a corresponding annuloplasty ring sizer, the surgeon is able to select an appropriate annuloplasty ring.

The anterior leaflet of the mitral valve is stretched for sizing by inserting a pair of nerve hooks into the proximate *chordae tendinae* and pulling the *chordae tendinae* in different directions via the pair of nerve hooks. The *chordae tendinae* are attached to the anterior and posterior papillary muscles surrounding the anterior leaflet and effectively prevent the anterior leaflet area from prolapsing into the left atrium during normal valve function. The anterior leaflet is position for sizing when the *chordae tendinae* are pulled by the nerve hooks.

Because each nerve hook requires one hand to pull the *chordae tendinae* in a specific direction, the sizing operation requires the use of three hands. As a result, the surgeon performing the procedure requires assistance from another person in a relatively small physical area during a delicate procedure. It would be advantageous to have an instrument that would allow a surgeon to properly pull the *chordae tendinae* with a single hand, thus leaving his or her other hand free for insertion of the annuloplasty ring sizer.

SUMMARY OF THE INVENTION

The present invention features an instrument for spreading an anterior leaflet of a mitral valve by pulling a *chordae tendinae* attached proximate the anterior leaflet. The instrument includes a pair of tines which each include an engagement tip. Each engagement tip is designed to engage the *chordae tendinae* proximate the anterior leaflet. Further, the pair of tines are coupled together by a resilient member, such that actuation of the resilient member moves one engagement tip relative to the other. In this manner, the *chordae tendinae* can be engaged at two locations and pulled outwardly to appropriately stretch the anterior leaflet for comparison of an annuloplasty ring sizer.

According to another aspect of the invention, a method is provided for using an instrument having a pair of tines designed to engage a *chordae tendinae* attached to anterior and posterior papillary muscles. This allows spreading of the leaflet of a heart valve for measurement. The method includes coupling the pair of tines to a mechanism that can be held by a single human hand. The method further includes engaging the pair of tines with a *chordae tendinae*, and separating the pair of tines to open the leaflet for measurement. The method further includes holding of the mechanism in the first hand of a user to permit freedom of the second hand in performing the desired leaflet measurements.

According to a further aspect of the invention, an instrument is provided that facilitates use of an annuloplasty ring sizer in determining an appropriately sized annuloplasty ring. The instrument includes a first tine having a first tip to engage tissue on the left side of the anterior leaflet. The instrument also includes a second tine having a second tip to further engage the tissue on the right side of the anterior leaflet. A gripping mechanism is coupled to the first tine and the second tine and permits a surgeon to hold the first tip at a desired distance or location relative to the second tip with a single hand. Thus, the surgeon can appropriately spread the anterior leaflet while one hand remains free to manipulate the annuloplasty ring sizer.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

Figure 1:
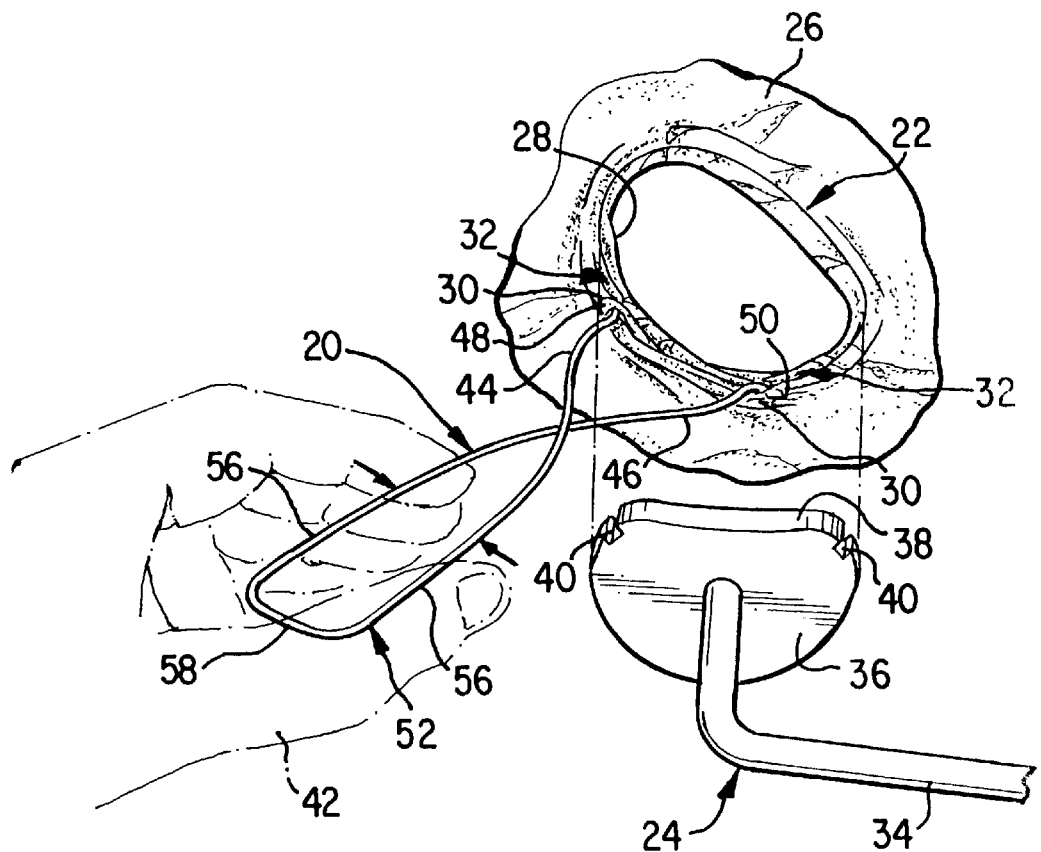
FIG. 1 is a perspective view of an instrument, according to a preferred embodiment of the present invention, engaged with tissue surrounding a subject heart valve.
Figure 2:
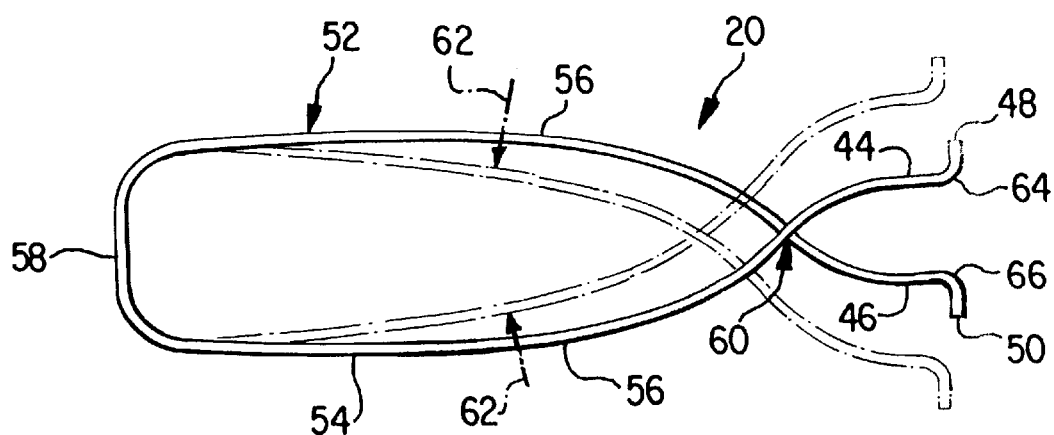
FIG. 2 is a front view of the instrument illustrated in FIG. 1 further showing the instrument in an actuated position via dashed lines.

Referring generally to FIGS. 1 and 2, an instrument 20 is illustrated according to a preferred embodiment of the present invention. Instrument 20 is designed to permit a surgical practitioner to retract and spread the anterior leaflet of a heart valve 22 for insertion of an annuloplasty ring sizer 24. One or more ring sizers 24 may be used to determine an appropriate size for an annuloplasty ring (not shown) to be implanted at heart valve 22.

In FIG. 1, a sketch of heart valve leaflet 22 is provided to facilitate understanding of the use of instrument 20. Specifically, heart valve leaflet 22 is part of a heart 26, such as a human heart undergoing implantation of an annuloplasty ring. Only a portion of heart 26 is illustrated, but the portion includes the exemplary heart valve 22. Valve 22 includes an anterior leaflet 28 that is connected by at least two series of *chordae tendinae* 30 to anterior and posterior papillary muscles 32. The anterior leaflet 28 may be stretched or opened for measurement by engaging the *chordae tendinae* 30 and preferably retracting and pulling the *chordae tendinae* 30 outwardly in different directions to spread anterior leaflet 28 and expose it for measurement via ring sizer 24.

In the illustrated embodiment, ring sizer 24 includes a handle or a shaft 34 that may be gripped by the surgeon or other practitioner performing the operation. Additionally, ring sizer 24 includes a sizing end 36 connected to a distal end of handle 34. Each ring sizer 24 has a sizing end 36 of a predetermined size that corresponds to the size of potential annuloplasty rings to be implanted. Further, sizing end 36 includes a perimeter edge 38 that has a contour generally matching the shape of a stretched or expanded anterior leaflet. Sizing end 36 further includes a pair of marker indentations 40 to facilitate alignment of sizing end 36 with anterior leaflet 28.

In FIG. 1, an exemplary embodiment of instrument 20 is illustrated in an engaged or actuated position at heart valve 22. As shown, a single hand 42 may be used to draw *chordae tendinae* 30 and papillary muscles 32 outwardly and in separate directions as anterior leaflet 28 is stretched for comparison with ring sizer 24. This leaves the practitioner's other hand free to grip handle 34 of annuloplasty ring sizer 24.

With additional reference to FIG. 2, instrument 20 includes a first tine 44 and a second tine 46. First tine 44 includes a first engagement tip 48, and second tine 46 includes a second engagement tip 50. Engagement tips 48 and 50 are designed to engage or hook under the *chordae tendinae* 30 at two unique locations, as illustrated in FIG. 1.

First tine 44 is coupled to second tine 46 by a gripping mechanism 52 appropriately sized for gripping and use in the single hand 42 of the practitioner. In the illustrated embodiment, gripping mechanism 52 comprises a resilient member 54 that is generally formed as a loop of resilient material. For example, resilient member 54 may be formed from a resilient metal material, such as spring steel, or a resilient plastic material acceptable for surgical procedures. The exemplary configuration of resilient member 54 includes a pair of force receiving sections 56 coupled together by a base portion 58 at an end opposite tines 44 and 46.

Opposite base portion 58, first tine 44 and second tine 46 are connected to force receiving sections 56 and oriented to cross one another at a cross section 60. Thus, when a sufficient force is applied to force receiving sections 56 in the inward direction as illustrated by arrows 62, resilient member 54 flexes and engagement tips 48 and 50 move apart.

As illustrated best in FIG. 2, when instrument 20 is in an unactuated, e.g. unflexed, state, engagement tips 48 and 50 are close or proximate one another, as illustrated in solid lines. It should be noted that in this embodiment, first tine 44 and second tine 46 include curved sections 64 and 66, respectively, which curve outwardly or away from one another. Thus, engagement tips 48 and 50 are oriented away from one another for engagement with the *chordae tendinae* 30. Further, when sufficient force is applied to resilient member 54 at force receiving sections 56, the engagement tips 48 and 50 are moved away from one another, as illustrated by dashed lines in FIG. 2.

The design of instrument 20 permits the surgeon to insert engagement tips 48 and 50 under the anterior leaflet *chordae tendinae* 30 and to squeeze resilient member 54 such that engagement tips 48 and 50 engage the *chordae tendinae* 30 at two unique and separate locations. By further squeezing force receiving sections 56, the surgeon is able to pull the *chordae tendinae* 30 in different directions and the tissue is pulled down and outwardly with the anterior leaflet 28, thereby spreading anterior leaflet 28 for measurement. Because of the unique design of instrument 20, engagement and pulling of the *chordae tendinae* 30, and resultant spreading of the anterior leaflet 28 for measurement, can be accomplished with a single hand, leaving the surgeon's other hand free for manipulation of annuloplasty ring sizer 24.

Figure 3:
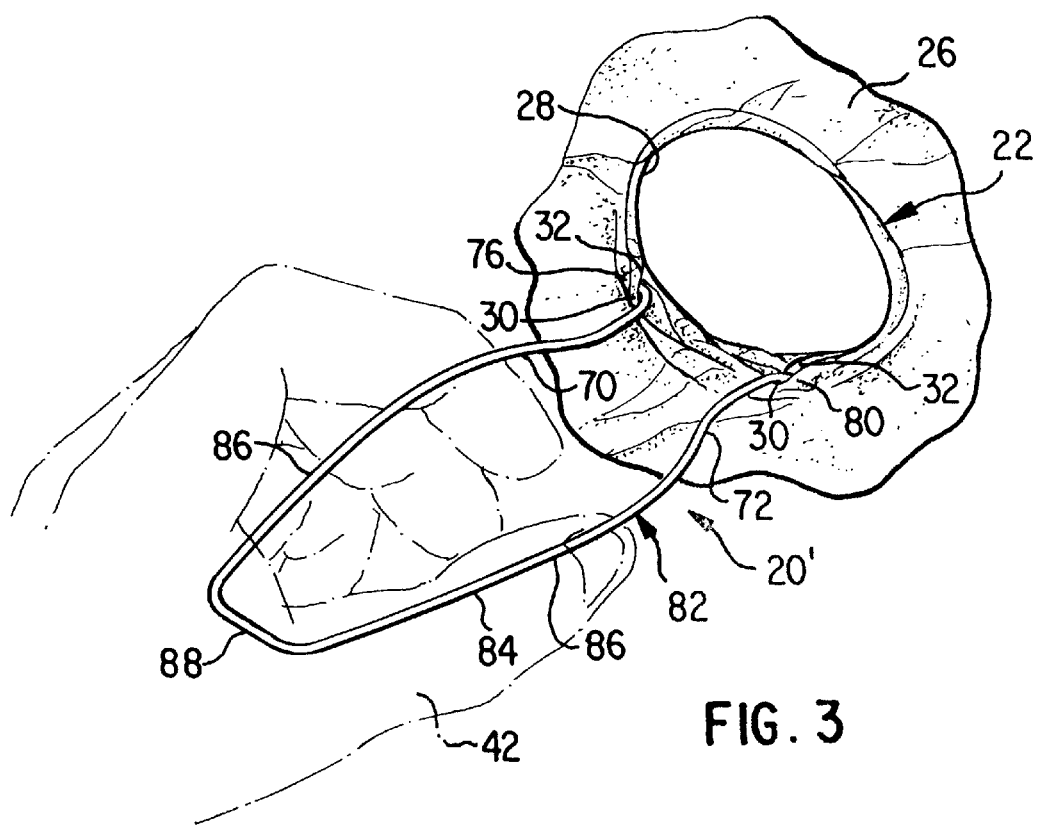
FIG. 3 is a perspective view of an alternate embodiment of the instrument illustrated in FIG. 1.
Figure 4:
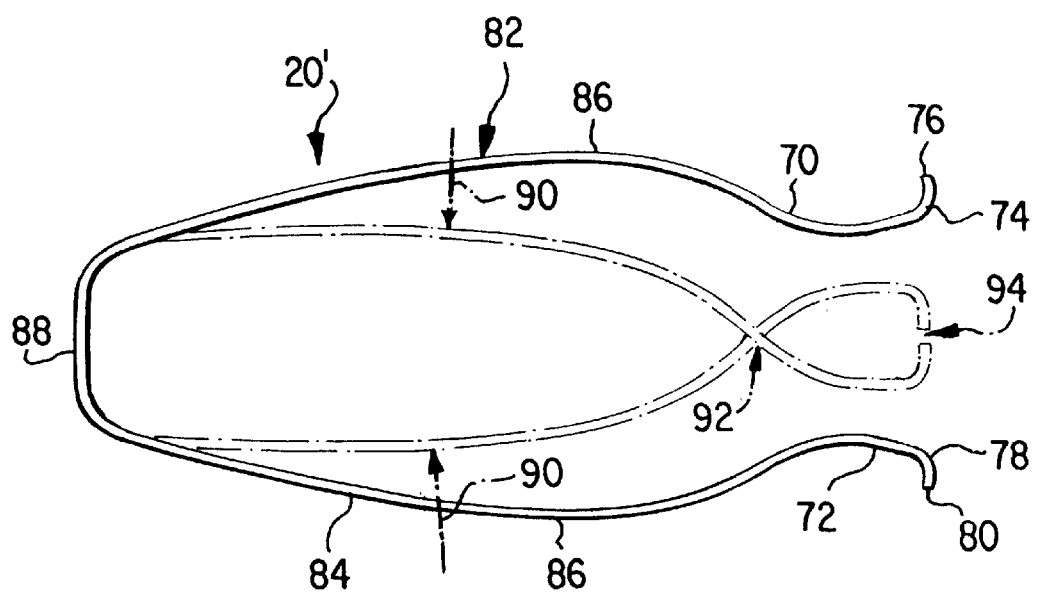
FIG. 4 is a front view of the instrument illustrated in FIG. 3 showing the engagement tines in two different positions.

An alternate embodiment of instrument 20, labeled 20', is illustrated in FIGS. 3 and 4. As illustrated, instrument 20' includes a first tine 70 and a second tine 72. First tine 70 includes a curved section 74 that terminates at a first engagement tip 76. Similarly, second tine 72 includes a curved section 78 that terminates at a second engagement tip 80.

First tine 70 and second tine 72 are connected to a gripping mechanism 82 including a resilient member 84. Resilient member 84 is formed by a pair of force receiving sections 86 that are coupled to a base portion 88 at one end and tines 70 and 72 at the opposite end.

In this embodiment, resilient member 84 holds engagement tips 76 and 80 in a separated or actuated position when unflexed. For insertion under the anterior leaflet chordae 30, gripping mechanism 82 must be squeezed with sufficient force to overcome the resiliency of resilient member 84 and to move engagement tips 76 and 80 into proximity with one another. The squeezing force is directed generally as indicated by arrows 90 until first tine 70 and second tine 72 cross at a cross section 92 illustrated in FIG. 4 via the flexed embodiment shown in dashed lines.

In the embodiment illustrated, curved sections 74 and 78 are oriented such that engagement tips 76 and 80 are directed away from one another or outwardly when applied to the *chordae tendinae* as illustrated in FIG. 3 or as illustrated in solid lines in FIG. 4. However, when resilient member 84 is flexed and force receiving sections 86 are moved inwardly along arrows 90, first tine 70 is preferably crossed with second tine 72 such that engagement tips 76 and 80 are directed towards a common area 94. This orientation of curve sections 74 and 78, and the location of engagement tips 76 and 80 upon movement of force receiving sections 86 along arrows 90, permits tines 70 and 72 to easily be inserted between the papillary muscles 32. Following insertion of instrument 20', engagement tips 76 and 80 are allowed to engage the *chordae tendinae* 30 by reducing the force acting on force receiving sections 56, i.e. the force applied by the surgeon's hand 42. The degree to which engagement tips 76 and 80, as well as the *chordae tendinae* 30, are spread can be controlled by the surgeon simply by allowing the natural resiliency of resilient member 84 to spread tines 70 and 72.

Figure 5:
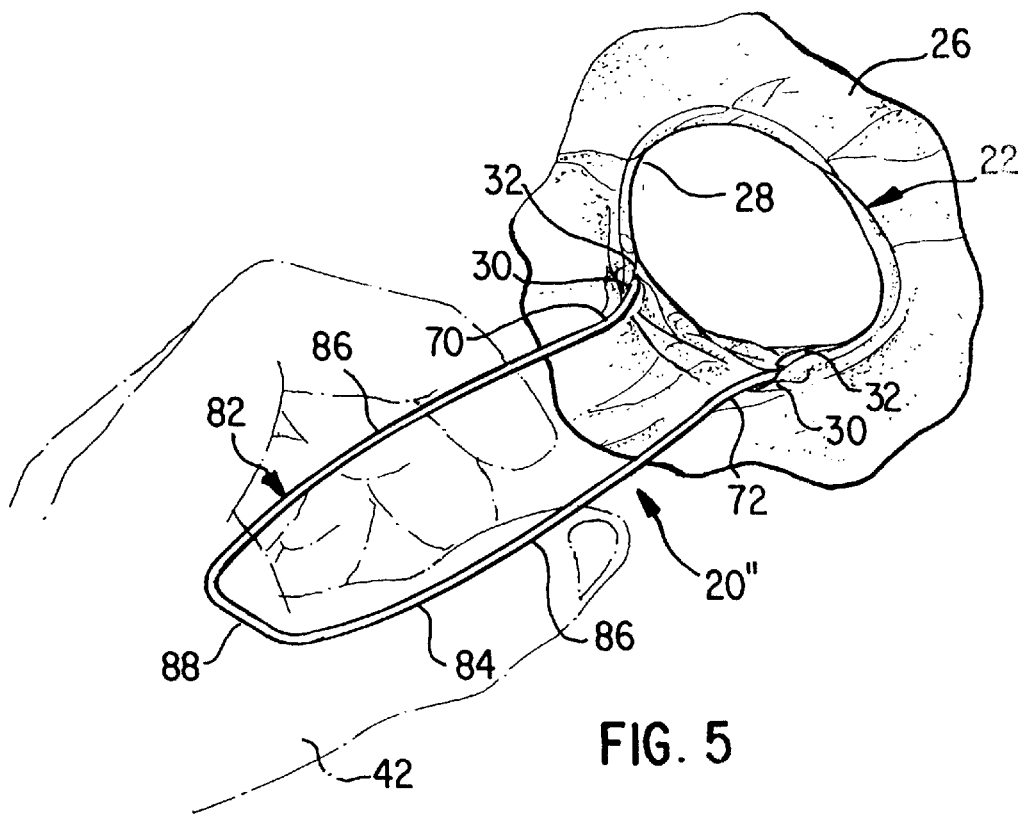
FIG. 5 is a perspective view of another embodiment of the instrument illustrated in FIG. 1.
Figure 6:
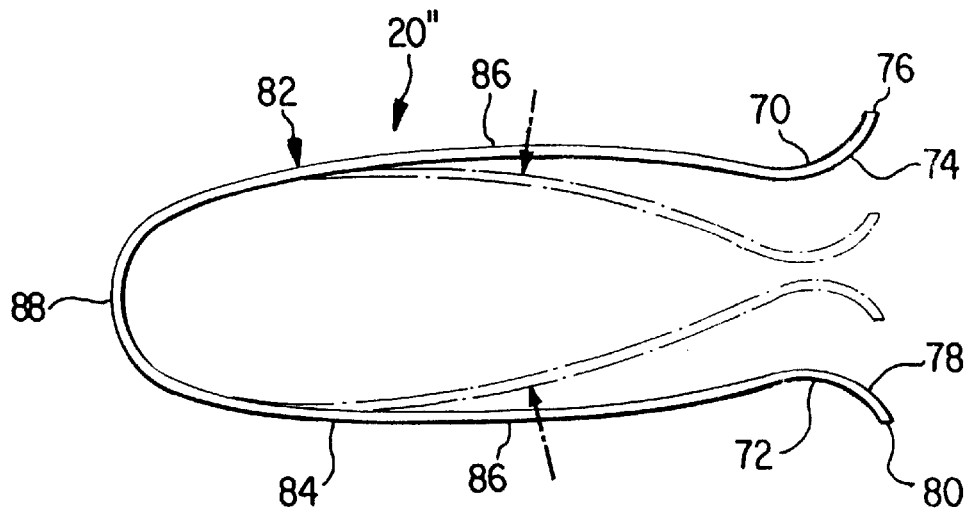
FIG. 6 is a front view of the instrument illustrated in FIG. 5.

Referring generally to FIGS. 5 and 6, another embodiment of instrument 20 is illustrated and labeled as 20". This embodiment is substantially similar to the embodiment illustrated in FIGS. 3 and 4 and the same reference numerals have been applied to similar elements. In this latter embodiment, however, first tine 70 and second tine 72 do not cross when force is applied to force receiving sections 86 along arrows 90. Further, engagement tips 76 and 80 remain oriented away from each other in an outward direction even when resilient member 84 is flexed for insertion of first tine 70 and second tine 72 between papillary muscles 32 to permit engagement of tips 76 and 80 with the *chordae tendinae* 30. (See instrument 20" in a flexed position shown in dashed lines in FIG. 6). As described with respect to the embodiment illustrated in FIGS. 3 and 4, the pulling or separating of the *chordae tendinae* 30 is controlled by permitting the natural resiliency of resilient member 84 to spread engagement tip 76 with respect to engagement tip 80.

Figure 7:
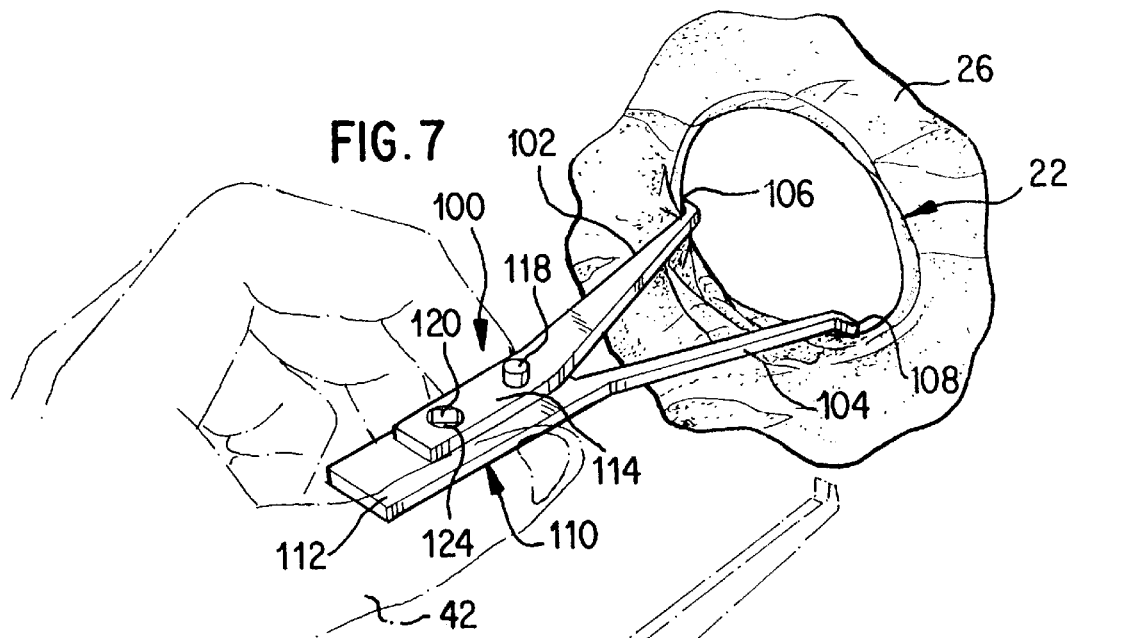
FIG. 7 is a perspective view of another embodiment of the invention illustrated in FIG. 1.
Figure 8:
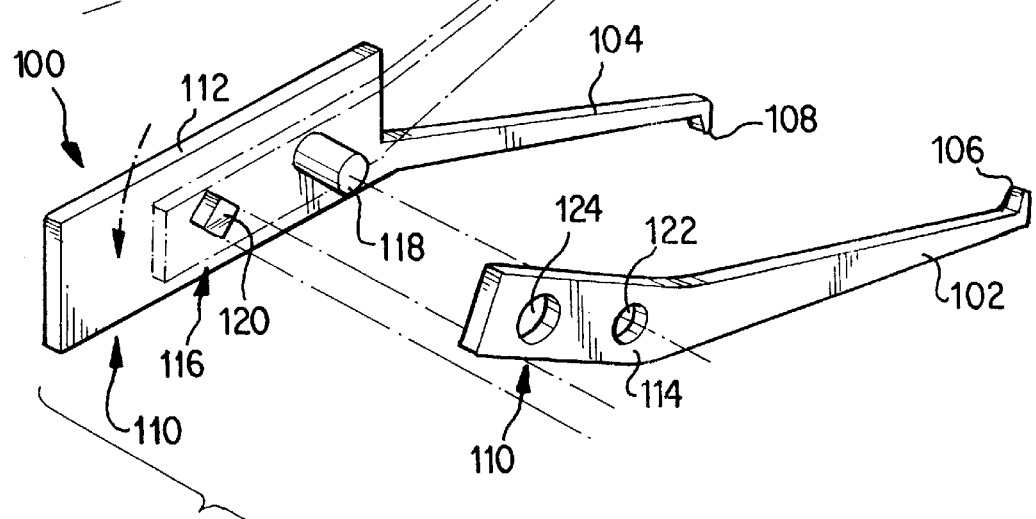
FIG. 8 is an exploded view of the instrument illustrated in FIG. 7.
Figure 9:
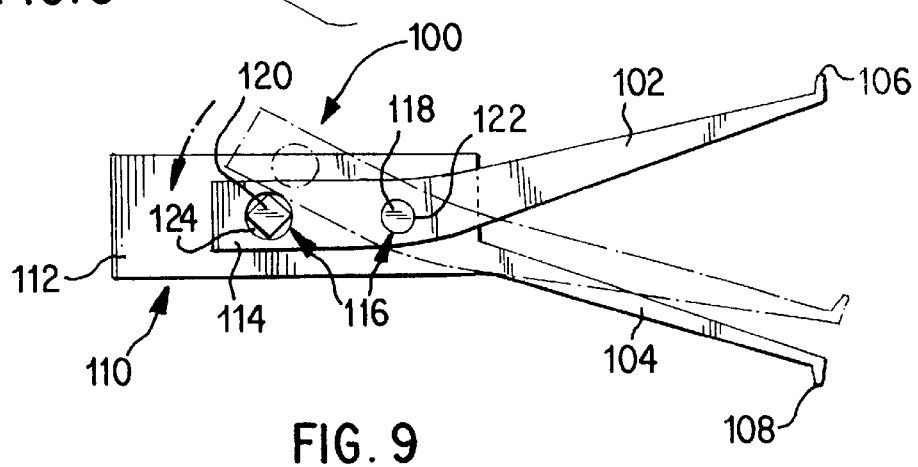
FIG. 9 is a front view of the instrument illustrated in FIG. 7.

Referring generally to FIGS. 7 through 9, another embodiment of instrument 20 is illustrated. In this embodiment, an instrument 100 includes a first tine 102 and a second tine 104. First tine 102 includes a first engagement tip 106, and second tine 104 includes a second engagement tip 108. Engagement tips 106 and 108 are utilized in spreading the anterior leaflet, as best illustrated in FIG. 7. First tine 102 and second tine 104 are connected to a gripping mechanism 110 designed to be held by the single hand 42 of a surgical practitioner.

As illustrated best in FIG. 8, first tine 102 and second tine 104 may be separated from one another. Specifically, gripping mechanism 110 is separable and includes a base component 112 connected to second tine 104 and an attachable component 114 connected to first tine 102. The separability of tines 102 and 104 may facilitate engagement and manipulation of tips 106 and 108 in certain procedures.

As illustrated, an interlocking mechanism 116 is used to couple and decouple base component 112 from attachable component 114. In the exemplary illustrated embodiment, interlocking mechanism 116 includes a front pin 118 and a rear pin 120. Front pin 118 and rear pin 120 extend laterally from base component 112, as illustrated. Further, interlocking mechanism 116 includes a corresponding front opening 122 and a corresponding rear opening 124 for receiving front pin 118 and rear pin 120, respectively. Front opening 122 and rear opening 124 are formed laterally through attachable component 114.

In the illustrated embodiment, front pin 118 is generally circular in cross section, and rear pin 120 is generally square or rectangular in cross section. Attachable component 114 may be coupled to base component 112 in a fixed position by inserting front pin 118 and rear pin 120 into front opening 122 and rear opening 124, respectively. During a procedure, engagement tips 106 and 108 may be engaged with the *chordae tendinae* and pulled to open the anterior leaflet, and then tines 102 and 104 may be locked into position by interlocking attachable component 114 to base component 112. Once coupled together, instrument 100 can readily be held in a single hand of the surgical practitioner, allowing the practitioner to utilize his or her free hand in measuring the anterior leaflet.

Optionally, circular front pin 118 may extend outwardly a greater distance than rear pin 120. This would allow attachable component 114 and first tine 102 to be rotated about front pin 118, as illustrated best in FIG. 9. Potentially, tines 102 and 104 could be rotated apart to spread the anterior leaflet and then locked in place by sliding rear pin 120 into rear opening 124.

It will be understood that the foregoing description is of preferred exemplary embodiments of this invention, and that the invention is not limited to the specific forms shown. For example, a variety of tine configurations and engagement tip configurations may be utilized; a variety of materials, such as a metallic and plastic material suitable for surgical instruments, may be used in the construction of the instruments; the gripping mechanisms may be made in various shapes and with various handles to facilitate holding of the instrument in a single hand; and the size and shape of the gripping mechanism may be adjusted to accommodate the desires of surgical practitioners. These and other modifications may be made in the design and arrangement of the elements without departing from the scope of the invention as expressed in the appended claims.

What is claimed is:

1. A method for using an instrument, having a pair of tines designed to engage a *chordae tendinae* attached to anterior and posterior papillary muscles, to spread a leaflet of a heart valve for measurement, comprising:

coupling a pair of tines to a gripping mechanism that can be held by a single human hand;

engaging the pair of tines with a *chordae tendinae*;

separating the pair of tines; and holding the mechanism in a first hand of a user while a second hand of the user remains free to perform measurements.

2. The method as recited in claim 1, further comprising forming the mechanism from a resilient member.

3. The method as recited in claim 2, further comprising moving the pair of tines to a position proximate one another prior to engaging the pair of tines with the *chordae tendinae*.

4. The method as recited in claim 2, wherein separating includes squeezing the resilient member to overcome its resilient bias and thereby separate the pair of tines.

5. The method as recited in claim 2, further comprising overcoming a biasing force of the resilient member to move the pair of tines towards one another prior to engaging the pair of tines with the *chordae tendinae*; and allowing the biasing force to facilitate separating the pair of tines following engaging the pair of tines with the *chordae tendinae*.

6. The method as recited in claim 1, further comprising forming the mechanism from a pair of separable members.

7. The method as recited in claim 6, further comprising providing the pair of members with a locking mechanism to hold the pair of tines at a desired, separated position.

8. The method as recited in claim 1, further comprising forming the mechanism from a metal material.

9. The method as recited in claim 1, further comprising forming the mechanism from a plastic material.

10. An instrument that facilitates use of an annuloplasty ring sizer in determining an appropriately sized annuloplasty ring for attachment proximate a valve of the heart, comprising:

a first tine having a first tip to engage tissue proximate an anterior leaflet;

a second tine having a second tip to engage tissue proximate the anterior leaflet;

a gripping mechanism to which the first tine and the second tine are connected wherein the gripping mechanism allows a practitioner to hold the first tip at a desired distance from the second tip while at least one hand of the practitioner remains free to manipulate the annuloplasty ring sizer, and said gripping mechanism comprising a plurality of separable components; said gripping mechanism further comprising an interlocking mechanism wherein said plurality of separable components can be selectively held together and positioned in a first open configuration or a second closed configuration by said interlocking mechanism, and wherein the plurality of components are interlocked during use of the annuloplasty ring sizer.

11. The instrument as recited in claim 10, wherein the interlocking mechanism comprises at least one pin and at least one opening for receiving the pin, at least one pin and at least one opening being formed in the plurality of components.

12. The instrument as recited in claim 10, wherein the gripping mechanism comprises a resilient member.

13. An instrument that facilitates use of an annuloplasty ring sizer in determining an appropriately sized annuloplasty ring for attachment proximate a valve of the heart, comprising:

a first tine having a first tip to engage tissue proximate an anterior leaflet;

a second tine having a second tip to engage tissue proximate the anterior leaflet;

a gripping mechanism having a first component to which the first tine is connected and a second component to which the second tine is connected wherein the gripping mechanism allows a practitioner to hold the first tip at a desired distance from the second tip while at least one hand of the practitioner remains free to manipulate the annuloplasty ring sizer, and an interlocking mechanism connecting the first and second components, the interlocking mechanism comprising at least one pin and at least one opening for receiving the pin, the at least one pin and the at least one opening being formed in said components.

14. An instrument that facilitates use of an annuloplasty ring sizer in determining an appropriately sized annuloplasty ring for attachment proximate a valve of the heart, comprising:

a first component having a first tine with a first tip to engage tissue proximate an anterior leaflet;

a second component having a second tine with a second tip to engage tissue proximate the anterior leaflet; and a coupling for selectively attaching said first component to said second component while said first component engages tissue, said coupling comprises a locking mechanism, wherein said locking mechanism comprises: a first pin mounted on said first component, a first hole in said second component, a second pin mounted on one of said first and second components, and a second hole in the other of said first and second components.

15. The instrument as recited in claim 13 wherein the first pin is longer than the second pin.

16. The instrument as recited in claim 13 wherein said second pin does not conform to said second hole.

17. The instrument as recited in claim 15 wherein said second pin has a square cross section and said second hole has a circular cross section.

18. The instrument as recited in claim 13 wherein said pin is between said locking apparatus and said tips.

19. The instrument as recited in claim 13 wherein the coupling further comprises a locking apparatus for interlocking said first component to said second component.

20. An instrument for retracting and spreading a heart valve leaflet, comprising:

a first tine having a first tip to engage tissue proximate an anterior heart valve leaflet;

a second tine having a second tip to engage tissue proximate the anterior leaflet;

a gripping mechanism to which the first tine and the second tine are connected, said gripping mechanism comprising a plurality of separable components and allowing a user to hold the first tip at a desired distance from the second tip with a single hand, and said gripping mechanism further comprising an interlocking mechanism wherein said plurality of separable components can be selectively held together and positioned in a first open configuration or a second closed configuration by said interlocking mechanism.

* * * * *